United States Patent [19]

Shipchandler

[11] 3,966,699

[45] June 29, 1976

[54] REDUCED BACITRACIN

[75] Inventor: Mohammed T. Shipchandler, Terre Haute, Ind.

[73] Assignee: Commercial Solvents Corporation, Terre Haute, Ind.

[22] Filed: Feb. 7, 1975

[21] Appl. No.: 548,124

[52] U.S. Cl. .................. 260/112.5 R; 424/177; 426/656
[51] Int. Cl.² .................. C07C 103/52; C07G 7/00
[58] Field of Search ............. 260/112.5 R; 424/177; 426/656

[56] References Cited
UNITED STATES PATENTS 3,795,663   3/1974   Miescher.................. 260/112.5 R
3,891,615   6/1975   Hodge et al................. 260/112.5 R Primary Examiner—Lewis Gotts
Assistant Examiner—Reginald J. Suyat
Attorney, Agent, or Firm—Robert H. Dewey; Howard E. Post

[57] ABSTRACT

Reduced bacitracin and pharmaceutically acceptable salts thereof obtained by treating bacitracin with a reducing agent. The resulting product has improved stability.

5 Claims, No Drawings

REDUCED BACITRACIN

BACKGROUND OF THE INVENTION

This application relates to reduced bacitracin and pharmaceutically acceptable salts thereof. In a particular aspect this application relates to reduced bacitracin having improved stability.

Bacitracin is an antibiotic obtained by cultivation of the organism Bacillus subtilis on a nutrient fermentation medium. It is a polypeptide containing a thiazoline ring as a portion of its structure. Bacitracin and its salts are effective against most bacteria but are relatively ineffective against fungi.

Bacitracin itself is rather unstable and its potency gradually diminishes on storage at ambient temperatures. This effect is especially significant at elevated temperatures. Salts of bacitracin are much more stable — especially the zinc salt — and have been valuable in animal feeds as growth promoters. However, stability is still a problem with such products, especially in the presence of moisture normally present in feed ingredients. Accordingly there is a need for a form of bacitracin which has improved stability during storage.

SUMMARY OF THE INVENTION

It is an object of this invention to provide a reduced form of bacitracin and its pharmaceutically acceptable salts.

It is another object of this invention to provide a reduced form of bacitracin having improved stability.

Other objects will be apparent to those skilled in te art from the description herein.

The present invention is to provide a reduced form of bacitracin wherein the thiazoline ring is converted to a thiazolidine ring. The resultant product surprisingly exhibits improved stability compared with bacitracin, and the zinc salt is particularly noteworthy.

DETAILED DISCUSSION

The reduced bacitracin and pharmaceutically acceptable salts thereof of this invention are provided by treating bacitracin with a suitable reducing agent for a length of time effective to reduce the thiazoline ring. After reduction the reduced bacitracin can be reacted with a zinc or manganese salt or with methylene disalicylic acid to provide a pharmaceutically acceptable salt. Methods for preparing these salts from the unreduced bacitracin are known in the art and the same methods can be used for preparing the salts of reduced bacitracin.

Preferably the bacitracin is treated with sodium borohydride in a ratio of about 1:1 by weight for a period of about 0.5 to about 1.5 hours or more, preferably about 1 hour at ambient temperature. Some cooling may be preferred to prevent a temperature rise. An aqueous solution is preferred for carrying out the reaction. After the reaction period, the reduced bacitracin is extracted from the aqueous solution with butanol.

The reduced product has the same utility and the same anti-bacterial spectrum as the parent product and the organisms display the same sensitivity. The stability of the reduced material is much improved, however. It is therefore especially useful in animal feeds.

The bacitracin suitable for the practice of this invention is commercially available and the usual commercial product is satisfactory. It need not be sterile. Similarly the usual commercial grade of sodium borohydride is satisfactory provided it does not introduce undesirable contaminants in the final product.

The invention will be better understood with reference to the following examples. It is understood that the examples are intended for illustration only, and it is not intended that the invention be limited thereby.

EXAMPLE 1

Bacitracin 5 g (3.52 mmol) was dissolved in 50 ml of water containing 1 ml of butanol as an antifoam. Sodium borohydride $NaBH_4$ 5 g (132 mmol) was added and the reaction mixture was stirred magnetically, under nitrogen at 25°C, for 1 hour (cooling of the reaction mixture was necessary to prevent a slight rise in the temperature). The mixture was neutralized at the end of the reaction period with concentrated phosphoric acid to lower the pH from 8 to 7. Addition of more antifoam agent (1 ml) was necessary during this process. The mixture was filtered to remove a white precipitate believed to be boric acid. The precipitate was washed with water (2 × 10 ml) and the washings were added to the filtrate.

The product was recovered using the extraction procedure of G. Miescher, U.S. Pat. No. 3,795,663, which is incorporated herein by reference thereto, as follows. The combined filtrate and washings were extracted with butanol (2 × 20 ml). The butanol phase was washed with water (2 × 20 ml) and the washings were discarded. It was then extracted with water and adjusted to pH 2 with phosphoric acid (2 × 10 ml). The aqueous phase was then adjusted to pH 6.5 with a calcium hydroxide slurry. The insoluble material was removed by filtration and the filtrate was concentrated to about 60% of the original volume. Lyophilization of the concentrate gave a white fluffy solid (1.2 g, yield 24%).

A sample of the original bacitracin and the reduced bacitracin were assayed and then tested for heat stability by heating at 105°C for 24 hours, then re-assaying. The results were as follows:

|  | Before Heating | Bioassay After Heating | Activity Retained | Ash |
| --- | --- | --- | --- | --- |
| Bacitracin | 63.4 μ/mg | 27.9 μ/mg | 44% | Nil |
| Reduced | 33.5 | 21.0 | 63 | 8.2% |

EXAMPLE 2

Bacitracin 40 g (28.4 mmol) was dissolved in 400 ml water containing butanol (24 ml). Sodium borohydride 40 g (1056 mmol) was added and the reaction mixture was stirred at 25°–30°C (cooling in a water bath was necessary). A 50 ml aliquot was withdrawn after 0.5 hour and adjusted to pH 7 with 50% phosphoric acid while cooling in an ice bath. The precipitate was collected on a filter and washed with butanol (20 ml). This butanol wash was then used in the extraction of the filtered aqueous phase. The aqueous layer was reextracted with butanol (20 ml). The combined butanol phase was washed with $H_2O$ (10 ml), the washing being discarded. Water (50 ml) was added to the butanol layer and the butanol was removed by azeotropic evaporation on a rotary evaporator. The aqueous solution of reduced bacitracin was lyophilized to yield a white fluffy powder (1.72 g).

Subsequent aliquots of 50 ml were taken at the intervals of 1 (3.4 g), 1.5 (2.6 g), 2 (2.6 g), 3 (3.4 g), 4 (3.5 g), 5 (2.5 g), and 6 hours (1.9 g) and worked up in the same fashion. The total product recovered weighed 21.5 g (54%).

A sample of the original bacitracin and a sample obtained from each of the aliquots were assayed, heated at 105°C for 24 hours, then re-assayed to determine heat stability. The results obtained are as follows:

Bioassay, $\mu$/mg

|  | Before Heating | After Heating | Activity Retained | Ash |
|---|---|---|---|---|
| Bacitracin | 60.2 | 10.2 | 17 | 0.1 |
| Reduced 0.5 hr. | 21.0 | 13.4 | 64 | 11.7 |
| 1 | 20.5 | 9.9 | 48 | 6.6 |
| 1.5 | 21.9 | 10.5 | 48 | 7.5 |
| 2 | 18.3 | 10.5 | 57 | 8.4 |
| 3 | 17.3 | 9.3 | 54 | 8.6 |
| 4 | 15.3 | 8.6 | 56 | 6.1 |
| 5 | 12.9 | 7.2 | 56 | 7.3 |
| 6 | 11.5 | 5.9 | 51 | 6.6 |

EXAMPLE 3

Reduced bacitracin (25 g) was dissolved in 300 ml of water. The solution was adjusted to pH 5 with hydrochloric acid diluted 1:2 with water. A freshly prepared 5% solution of zinc chloride (45 ml) was added with stirring. The pH dropped to 4.5 and a precipitate appeared. The turbid solution was clarified by the addition of dilute hydrochloric acid (1:2); the pH dropped to 4. Sodium hydroxide solution (5%) was added slowly to the filtered solution with vigorous agitation until the pH rose to 6.8. The resulting slurry was warmed to 50°C with stirring, then cooled to 30°C. A precipitate was collected from this slurry and washed twice with water. Most of the water was removed by suction and the light yellow product was dried overnight at 70°C in a vacuum oven. This gave a shiny glassy yellow substance (16 g) which seemed to have melted during drying.

A sample of the zinc salt of reduced bacitracin was assayed, heated at 105°C for 24 hours then reassayed. It retained 79% of its original activity, compared with 70% for a sample of commercial zinc bacitracin. It is used as a growth promoter in animal feeds in accordance with Chornock, U.S. Pat. No. 2,809,892 which is incorporated herein by reference thereto.

EXAMPLE 4

The procedure of Example 3 was repeated on a larger scale of reduced bacitracin. An aluminum coil was used for quick raising and lowering of the temperature. The final yellow product (463 g) was obtained by lyophilization rather than vacuum drying as in Example 3. The material assayed 28.1 u/mg and retained 64% of its activity through the heat test.

EXAMPLE 5

Reduced bacitracin (25 g) was dissolved in 300 ml of water and adjusted to pH 4 with dilute hydrochloric acid (1:2). A 5% solution of manganese chloride ($MnCl_2$) was added with stirring. The pH was then adjusted to 7.5 with 5% sodium hydroxide solution. The gummy precipitate was obtained which was washed twice by trituration with water. Freeze-drying of this gum gave a light gray powder (11.2 g).

This material assayed 31.8 u/mg. It retained 37% of its original activity after the thermal stability test.

EXAMPLE 6

Reduced bacitracin (20 g in 1500 ml($H_2O$) was complexed with 5,5'-methylenedisalicyclic acid (2.9 g dissolved in 100 ml 2% sodium hydroxide solution). The dark yellow solution was filtered and acidified with stirring with concentrated hydrochloric acid to pH 4. The precipitate was removed by filtration, washed with water and dried over phosphorus pentoxide in vacuum to yield a yellow powder (11.4 g). The material assayed 23.2 u/mg and retained 66% of its activity after the heat test.

I claim:

1. Reduced bacitracin and pharmaceutically acceptable salts thereof obtained by reacting bacitracin with sodium borohydride at ambient temperatures in a ratio of about 1:1 by weight and for a period of time of from about 0.5 to 1.5 hours.

2. The reduced bacitracin of claim 1 wherein the bacitracin is reacted with the sodium borohydride for a period of time of about 1 hour.

3. The zinc salt of the reduced bacitracin of claim 1.

4. The manganese salt of the reduced bacitracin of claim 1.

5. The methylene disalicylate salt of the reduced bacitracin of claim 1.

* * * * *

UNITED STATES PATENT OFFICE
CERTIFICATE OF CORRECTION

Patent No. 3,966,699   Dated June 29, 1976

Inventor(s) Mohammed T. Shipchandler

It is certified that error appears in the above-identified patent and that said Letters Patent are hereby corrected as shown below:

Column 1, line 32, "te" should read -- the --

Column 4, line 24, "(20 g in 1500 ml ($H_2O$) should read -- (20 g in 1500 ml $H_2O$) --

Signed and Sealed this twelfth Day of July 1977

[SEAL]

Attest:

RUTH C. MASON
*Attesting Officer*

C. MARSHALL DANN
*Commissioner of Patents and Trademarks*